United States Patent [19]

Reinicke

[11] E Re. 31,121

Best Available Copy [45] Reissued Jan. 11, 1983

[54] CONTROL DEVICE FOR PROSTHETIC URINARY SPHINCTER CUFF

[75] Inventor: Robert H. Reinicke, Mission Viejo, Calif.

[73] Assignee: Parker-Hannifin Corporation, Cleveland, Ohio

[21] Appl. No.: 176,546

[22] Filed: Aug. 8, 1980

Related U.S. Patent Documents

Reissue of:

[64] Patent No.: 4,167,952
Issued: Sep. 18, 1978
Appl. No.: 884,864
Filed: Mar. 9, 1978

[51] Int. Cl.[3] ..... F16K 17/18; A61B 17/00; A61F 1/00

[52] U.S. Cl. ..... 137/493; 3/1; 128/1 R; 128/DIG. 25

[58] Field of Search ..... 128/1 R, 346, DIG. 25; 3/1; 137/493, 522

[56] References Cited

U.S. PATENT DOCUMENTS

| | | | |
|---|---|---|---|
| 2,455,859 | 12/1948 | Foley | 128/346 |
| 2,533,924 | 12/1950 | Foley | 128/346 |
| 3,863,622 | 2/1975 | Buuck | 128/1 R |
| 3,946,755 | 3/1976 | Ulanovsky | 137/493 |
| 4,056,095 | 11/1977 | Rey et al. | 128/1 R |
| 4,106,510 | 8/1978 | Hakim et al. | 128/350 V |
| 4,116,201 | 9/1978 | Shah | 128/349 BV |
| 4,222,377 | 9/1980 | Burton | 128/1 R |
| 4,256,093 | 3/1981 | Helms et al. | 128/1 R |

*Primary Examiner*—Dalton L. Truluck
*Attorney, Agent, or Firm*—Maky, Renner, Otto & Boisselle

[57] ABSTRACT

A device for controlling flow of fluid to and from a resilient inflatable cuff implanted about the urethra to control flow of urine therethrough. The device comprises a flexible bulb reservoir and a control unit that includes a manually operated valve that opens automatically when the bulb is squeezed to force fluid into the cuff for closing the urethra. The control unit also includes a movable valve seat member having a relatively large area exposed to pressure of fluid in a chamber that is connected to the cuff and which moves to a position in which the valve member is unseated by an abutment when fluid pressure in the chamber exceeds a predetermined value to thereby relieve excess fluid pressure in the cuff. The arrangement is such that the valve element is held closed against the seat member by the full differential in fluid pressures acting on both sides of the valve element until the seat member is moved away from the valve element to thus insure positive closing of the valve element until the seat member is moved out of engagement with the valve element by excess pressure differential.

27 Claims, 6 Drawing Figures

CONTROL DEVICE FOR PROSTHETIC URINARY SPHINCTER CUFF

Matter enclosed in heavy brackets [ ] appears in the original patent but forms no part of this reissue specification; matter printed in italics indicates the additions made by reissue.

BACKGROUND OF THE INVENTION

*The invention described herein was made in the performance of work under NASA Contract No. NAS* 8-32970 and is subject to the provisions of section 305 of the National Aeronautics and Space Act of 1958 (72 Stat. 435; 42 U.S.C. 2457).

Various devices have been proposed for implantation in the human body for opening and closing the urethra when the sphincter muscle is unable to perform this function. Some of such devices are shown in U.S. Pat. Nos. 3,744,063, 3,863,622, 3,854,469, 3,903,894, and 4,019,499. They include a resilient inflatable cuff or other member that is implanted to surround the urethra and which when inflated by a fluid squeezes the urethra closed and when deflated permits the urethra to open.

In one such prior device as yet unpublished there is a bulb of flexible material that comprises a reservoir for the fluid and a valved control unit to control flow of fluid in both directions between the cuff and reservoir. The control unit includes a spring seated valve element that may be unseated by an abutment through manual operations to permit flow of fluid from the cuff to the reservoir and wherein the valve seat is movable by pressure of fluid within the reservoir to a position away from the valve element when the valve element is against the abutment to permit flow of fluid to the cuff. The valve element is also unseatable by excess fluid pressure in the cuff to thus act as a pressure relief valve. However, the arrangement is such that the spring force for seating the valve element is gradually overcome by the increasing differential in fluid pressure between the cuff and reservoir so that there is a diminishing seating force on the valve element as the relief pressure is approached. This results in less assurance that the valve will remain closed prior to the time that excess pressure in the cuff is experienced and hence leakage across the valve and opening of the urethra may occur at inconvenient times.

SUMMARY OF THE INVENTION

The present invention is an improvement in the prior device described above in that not only does the spring for closing the valve element exert its full force for maintaining the valve element closed prior to the time that excess pressure is developed in the cuff, but in addition the fluid pressure differential between the cuff and reservoir when the cuff pressure is greater than that in the reservoir supplements the spring pressure in maintaining the valve element closed until the pressure in the cuff exceeds a predetermined value.

This is accomplished by arranging the valve element so that it will be openable against pressure of its spring by pressure of fluid from the reservoir and seatable by pressure of fluid in the cuff, and by providing a movable seat member which has a relatively large area exposed to pressure of fluid from the cuff to move the seat member away from the valve element when the fluid pressure in the cuff is excessive and following movement of the valve element with the movable member is prevented by engagement of the valve element with an abutment.

BRIEF DESCRIPTION OF THE DRAWINGS

As shown in FIG. 1, the device 10 of the present invention is connected by a tube 11 to an inflatable cuff 12. All these parts are implanted surgically into a human body. Cuff 12 is a hollow donut shaped member of resilient flexible material such as a silicone elastomer and surrounds the urethra 13. Device 10 is preferably implanted within the scrotum of male patients where it is readily accessible for digital manipulation or it may be implanted at other locations in the body where it may be actuated by externally applied pressure.

Figure 3:
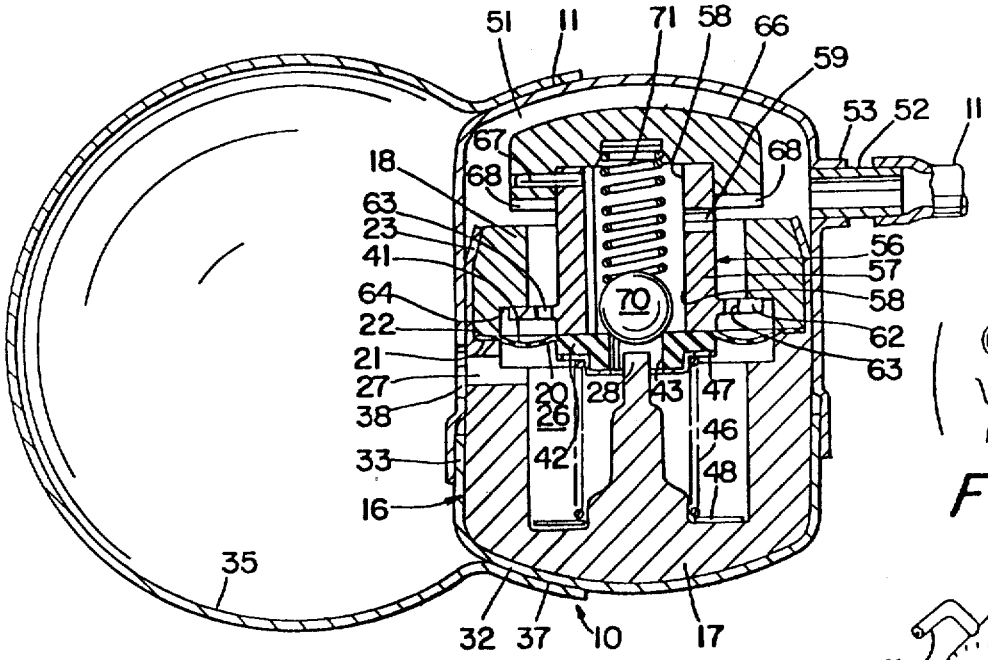
FIG. 3 is a cross-section view of the device in its normally closed position for trapping fluid under pressure in the cuff as when the latter is inflated for closing the urethra.
Figure 1:
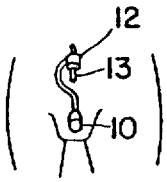
FIG. 1 is a view of the device as implanted in a human body.
Figure 2:
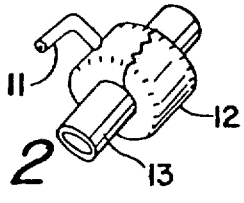
FIG. 2 is a view of the cuff.

Device 10 has a housing 16 that comprises a body 17 of nylon or other material and a ring 18 of nylon or the like that clamps a flexible diaphragm 20 at its outer margin 21 against a shoulder 22 on body 17. Ring 18 is retained by an inwardly crimped tubular extension 23 on body 17. Housing 16 has a cavity 26 with a duct 27 leading therefrom and also has an upwardly projecting abutment 28.

Cemented to tubular extension 23 is a cover 31 of flexible sheet material, such as silicone elastomer. Cover 31 is also cemented to another cover portion 32 of like material and which is also cemented to body 17, at least around the open end portion 33 of cover 32. A bulb shaped reservoir 35 of like flexible sheet material is cemented to cover portions 31, 32 as shown at 36,37. An opening 38 in cover portion 31 permits free communication between duct 27 and the interior of reservoir 35.

Diaphragm 20, which may also be made of a silicone elastomer, has a thin flexible peripheral portion 41 and a relatively thick non-flexible central portion 42 with an opening 43 therethrough. A spring 46 urges diaphragm central portion 42 upwardly and there are washers 47,48 between the spring and diaphragm portion 42 and body 17.

The interior of cover 31 forms a chamber 51 which communicates with a tubular member 52 which is cemented to a short tubular projection 53 on cover 31 and to which tube 11 is to be connected.

Mounted on housing 16 within chamber 51 is a plunger 56 comprised of a tubular member 57 having a bore 58, a side opening 59 and a flange 62 that has a series of circumferentially spaced holes 63 therethrough. Flange 62 overlaps shoulder 64 on ring 18 so that shoulder 64 acts as a stop to limit upward movement of plunger 56. Plunger 56 also includes a button 66 pinned to member 57 at 67 and whose lower face has radial grooves 68. Button 66 radially overlaps ring 18 to abut the latter for limiting downward movement of the plunger 56. Within bore 58 is a ball valve element 70 pressed by a relatively light spring 71 toward a seated position on diaphragm central portion 42 to control flow of fluid through port 43. Spring 46 is stronger than spring 71 so that diaphragm 20 central portion 42 is normally maintained against tubular member 57 and the latter in its upward position with flange 62 against shoulder 64.

OPERATION

During or before implantation, device 10 is completely filled with a liquid, such as a saline solution, so that reservoir 35 and all the spaces within housing 16, plunger 56 and chamber 51 are filled but not under pressure. Likewise tube 11 and cuff 12 are filled with the liquid but not under pressure. At this time the parts of device 10 are in the position shown in FIG. 3 with valve element 70 seated against diaphragm central portion 42, the latter against plunger member 57 and with flange 62 against shoulder 64. Cuff 12 will be deflated, that is, full of liquid that is not under pressure, so that urethra 18 will be open.

Figure 5:
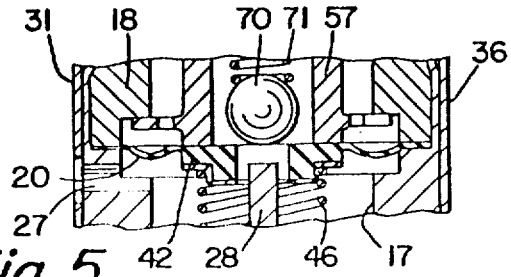
FIG. 5 is a fragmentary cross-section view showing the valve element in open position due to squeezing of the flexible reservoir.

To close the urethra, reservoir 35 is squeezed by digital manipulation to pressurize the liquid therein and force a portion thereof through duct 27 and cavity 26 to port 43 where it forces valve element 70 off its seat as in FIG. 5, and passes through bore 58, opening 59, chamber 51 and tube 11 to inflate cuff 12 for closing the urethra. Upon release of reservoir 35 and the consequent drop of pressure therein, valve element 70 will reseat to close opening 43 to trap pressurized liquid within bore 58, chamber 51, tube 11 and cuff 12 so that the latter remains inflated and the urethra closed.

Figure 4:
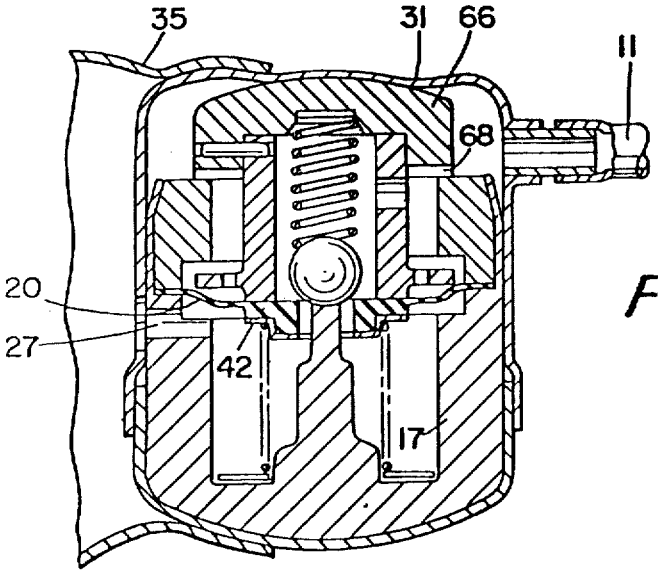
FIG. 4 is a cross-section view of the device when manually actuated for deflating the cuff to open the urethra.

To open the urethra, digital pressure is applied to covers 31,32 on vertical opposite sides of the device until cover 31 engages the upper surface of button 66. Plunger 56 is moved downward until the button engages ring 18, as in FIG. 4. In this position, projecting abutment 28 will have engaged valve element 70 to unseat the latter and permit fluid under pressure from above the valve element to flow through port 13 to the unpressurized cavity 26 and reservoir 35 to thus deflate cuff 12 and permit the urethra to open. Upon such release of pressure above valve element 70 the latter will again close. To reclose the urethra, digital pressure is again applied to the reservoir for inflating the cuff as already described.

Figure 6:
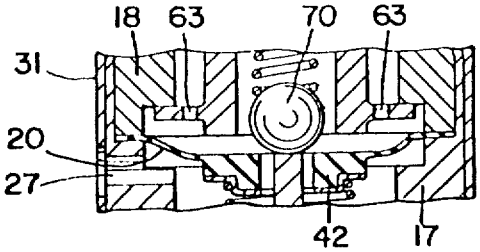
FIG. 6 is a fragmentary cross-section view showing the seat member when automatically moved away from the valve element to relieve excess pressure in the cuff.

In case too much digital pressure is applied to the reservoir, either intentionally or accidentally, excessive liquid pressure may be transmitted to the cuff. Upon release of the reservoir such excess pressure will be relieved by action of diaphragm 20. Thus, upon release of the reservoir, valve element 70 will close but the excess pressure in chamber 51 having access to the upper side of diaphragm 20 through holes 63 and the interior of bore 58, where it also acts downwardly on valve element 70, will force the diaphragm and valve element downwardly. When the valve element strikes abutment 28 its downward motion ceases but the diaphragm will continue downwardly so that its central portion 42 moves away from the valve element to open part 43, as shown in FIG. 6, and permit downward flow of liquid therethrough until the pressure of liquid in shoulder 51 and cuff 12 has a predetermined differential or value with respect to the pressure in reservoir 35 and cavity 26, as determined by springs 71 and 46. Thereupon spring 46 will raise diaphragm 20 to reseat against valve element 70 to trap liquid at the correct pressure in chamber 51 and cuff 12 according to the predetermined pressure differential.

With the present arrangement of device 10, when valve element 70 is closed to trap liquid under pressure in cuff 12 and chamber 51, this pressure which is supplemental by the force of spring 71, acts downwardly on the valve element across an effective area equal to the area bounded by its seating contact with diaphragm central portion 42, which is essentially the cross-section area of port 43 in this case. The full force of this downward fluid and spring pressure is maintained for keeping the valve element tightly seated at all times until the valve element is unseated by contact with abutment 28 either because of manual operation or of pressure relief action of the diaphragm. Such full force on the valve element eliminates the possibility of leakage past the valve element due to reduced seating pressure as occurs in the prior device described above. Also, because the effective area of the diaphragm subject to pressure of liquid within chamber 51 and plunger bore 58 is relatively large the diaphragm will be sensitive to pressure differentials exceeding the predetermined value and result in quick opening of part 43 for relieving the excess pressure in chamber 51 and cuff 12.

Although one specific form of the invention has been illustrated in the drawings, it is obvious that various modifications may be made within the scope of the invention as claimed. Thus, for example, diaphragm 20 could be replaced by a piston of rigid material with appropriate changes in body 17, tubular member 57 could be in the form of several rods, and so forth.

I claim:

1. A device useful with a prosthetic [urinary sphincter valve] *inflatable implant* for controlling flow of fluid from a reservoir to a receiver, said device comprising an envelope with a movable wall portion and which envelope is closed except for a first duct connectable to the reservoir and a second duct connectable to the receiver, a control unit in said envelope, said unit including a valve element and a ported seat member for controlling flow of fluid between said ducts, said seat member being spring pressed to a first position in which said valve element may be spring pressed into engagement *with* the seat member for closing the port therein, manually operable means for moving the seat member to a second position, means to prevent the valve element from seating on the seat member when the seat member is in said second position whereby the port in the seat member will be open, and said seat member having an effective area subject to pressure of fluid in said second duct and movable thereby to said second position.

2. The device of claim 1 in which the control unit includes an abutment engageable with the valve element when the seat member is in the second position.

3. The device of claim 1 in which the force of the spring for the seat member is greater than that of the spring for the valve member and acts in opposition thereto.

4. The device in claim 1 in which the seat member comprises a diaphragm having a flexible peripheral portion sealingly attached to the control unit and a relatively inflexible portion through which said port extends.

5. A device useful with a prosthetic [urinary sphincter valve] *inflatable implant* for controlling flow of fluid to and from a receiver, comprising a reservoir for fluid, a flexible cover and a control unit, said unit including a housing having a sealed connection to the cover to form a chamber therebetween, a duct leading from said chamber for connection to the receiver, the housing having an abutment and having a cavity and carrying a movable valve seat member that separates the cavity from the chamber, a port through the member for connecting the cavity to the chamber, a valve element, a first spring urging the valve element into engagement with the member for closing the port, a second spring urging the member to a first position in which the valve element is out of engagement with said abutment and in its port closing position, manually operable plunger for moving the seat member to a second position in which the abutment engages the valve element for opening said port, and said seat member having an area exposed to fluid in said chamber and movable thereby to its second position when the pressure of fluid in said chamber exceeds a predetermined value.

6. The device of claim 5 in which there is a stop to limit movement of the seat member in the direction toward its first position.

7. The device of claim 5 in which there is a stop to limit movement of the plunger in the direction toward said second position.

8. The device of claim 5 in which the seat member comprises a flexible diaphragm.

9. The device of claim 8 in which the diaphragm has a relatively thick central portion through which said port extends and a relatively thin and readily flexible peripheral portion.

10. The device of claim 9 in which said second spring bears against said central portion.

11. The device of claim 9 in which said plunger is engageable with said central portion.

12. The device of claim 5 in which said plunger has a bore and said valve element is within said bore.

13. The device of claim 5 in which said abutment projects into said port when the seat member is in said second position.

14. The device of claim 6 in which said stop comprises engagement of a portion of the plunger with a portion of said housing.

15. The device of claim 7 in which said stop comprises engagement of a portion of the plunger with a portion of said housing.

16. The device of claim 5 in which said valve element has an effective area subject to pressure fluid in said chamber for urging the valve element against the seat member for closing said port when the member is in said first position.

17. The device of claim 5 in which said plunger has a recess at one end thereof, said valve element is in said recess, said one end engages the seat member, and said plunger has a flange engageable with a shoulder on said housing to limit movement of the plunger in the direction of said first position.

*18. A device useful with a prosthetic inflatable implant for controlling flow of fluid from a reservoir to a receiver, said device comprising an envelope with a movable wall portion and which envelope is closed except for a first duct connectable to the reservoir and a second duct connectable to the receiver, a control unit in said envelope, said unit including a valve element and a ported seat member for controlling flow of fluid between said ducts, said seat member being spring pressed to a first position in which said valve element may be spring pressed into engagement with said seat member for closing the port therein, said valve element including an effective area subject to pressure of fluid in said first duct and movable thereby away from said seat member, manually operable means for moving said seat member to a second position, means to prevent said valve element from seating on said seat member when said seat member is in such second position whereby the port in seat said member will be open, and said seat member having an effective area subject to pressure of fluid in said second duct and movable thereby to such second position.*

*19. A device useful with a prosthetic inflatable implant for controlling flow of fluid from a reservoir to a receiver, said device comprising an envelope with a movable wall portion and a control unit in said envelope, said envelope having a first duct connectable to the reservoir and a second duct connectable to the receiver, and said control unit including a movable valve element and a movable ported valve seat member for controlling flow of fluid between said ducts, spring means for urging said seat member to a first position in which said valve element normally may be spring pressed into engagement with said seat member for closing the port therein, said valve element including an effective area subject to pressure of fluid in said first duct and movable thereby away from said seat member, means adapted to extend through said port into engagement with said valve element for unseating said valve element to open the port, said seat member having an effective area subject to pressure of fluid in said second duct and movable thereby from said first position to a second position in which said means for unseating extends through the port to unseat said valve element, and means responsive to movement of said movable wall portion for effecting relative movement of said seat member and means for unseating to a positional relationship in which said means for unseating extends through the port to unseat said valve element.*

*20. A device useful with a prosthetic inflatable implant for controlling flow of fluid from a reservoir to a receiver, said device comprising an envelope with a movable wall portion and a control unit in said envelope, said envelope having a first duct connectable to the reservoir and a second duct connectable to the receiver, and said control unit including a housing having an abutment and a cavity therein, a movable valve seat member in said housing dividing said cavity into first and second chambers, means connecting said first and second chambers respectively to said first and second ducts, said seat member having port means therein for connecting said first and second chambers, a valve element, first biasing means urging said valve element into engagement with said seat member for closing said port means, said valve element including an effective area subject to pressure of fluid in said first chamber and movable thereby against said first biasing means away from said seat member to open said port means, second biasing means for urging said seat member to a first position in which said valve element normally is out of engagement with said abutment, said seat member having an area exposed to fluid in said second chamber and movable thereby against said second biasing means to a second position in which said abutment engages said valve element to unseat same for opening said port means when the pressure of fluid in said second duct exceeds a predetermined value, and means responsive to said movable wall portion for unseating said valve element to open said port means independently of the fluid pressure level in said first and second chambers.*

*21. The device of claim 20 in which said means for unseating includes manually operable means for effecting relative movement of said seat member and abutment to a positional relationship in which said abutment engages said valve element to open said port means.*

*22. The device of claim 21 in which there are spring means for urging said valve seat and means for unseating out of such positional relationship.*

*23. The device of claim 19 or 20 in which the effective area of said seat member is greater than that of said valve element.*

*24. A device for controlling flow of fluid to and from a prosthetic inflatable implant, comprising a reservoir, an outlet duct connectable to the inflatable implant, and control means for controlling flow of fluid between said reservoir and outlet duct, said control means including passage means connecting said reservoir and outlet duct, first means for normally closing said passage means, said first means having an effective area subject to pressure of fluid in said reservoir and movable thereby for opening said passage means, second means having an effective area greater than that of said first means subject to pressure of fluid in said outlet duct and movable thereby from a first position for permitting said first means to close said passage means to a second position for preventing said first means to close said passage means when the pressure of fluid in said outlet duct exceeds a predetermined valve, and manually actuable means for moving said second means to its second position.*

*25. The device of claim 22 in which said second means includes a diaphragm.*

*26. The device of claim 22 in which there is an envelope for said control means, said envelope having a movable wall portion and said manually actuable means being responsive to manual movement of said movable wall portion.*

*27. The device of claim 22 in which said first means when closed further has an effective area subject to pressure in said outlet duct and is arranged such that said first means normally is held closed by the full fluid pressure differential between said reservoir and outlet duct.*

* * * * *